US007175841B2

(12) United States Patent
Badylak et al.

(10) Patent No.: US 7,175,841 B2
(45) Date of Patent: *Feb. 13, 2007

(54) ENHANCED SUBMUCOSAL TISSUE GRAFT CONSTRUCTS

(75) Inventors: Stephen F Badylak, West Lafayette, IN (US); Christina Lindberg, West Lafayette, IN (US); George B. Boder, Martinsville, IN (US); Sherry Voytik-Harbin, Zionsville, IN (US)

(73) Assignee: Purdue Research Foundation, West Lafayette, IN (US)

( * ) Notice: Subject to any disclaimer, the term of this patent is extended or adjusted under 35 U.S.C. 154(b) by 401 days.

This patent is subject to a terminal disclaimer.

(21) Appl. No.: 10/272,679

(22) Filed: Oct. 17, 2002

(65) Prior Publication Data
US 2003/0064056 A1  Apr. 3, 2003

Related U.S. Application Data

(60) Division of application No. 09/566,497, filed on May 8, 2000, now Pat. No. 6,485,723, which is a continuation of application No. 09/151,790, filed on Sep. 11, 1998, now abandoned, which is a continuation-in-part of application No. 08/530,002, filed on Sep. 19, 1995, now Pat. No. 5,866,414, and a division of application No. 08/386,452, filed on Feb. 10, 1995, now Pat. No. 5,695,998.

(51) Int. Cl.
*A61L 27/00* (2006.01)
(52) U.S. Cl. .................................. 424/93.7
(58) Field of Classification Search ................ 424/93.7
See application file for complete search history.

(56) References Cited

U.S. PATENT DOCUMENTS

| 4,439,521 A | 3/1984 | Archer et al. |
| 4,703,108 A | 10/1987 | Silver et al. |
| 4,743,552 A | 5/1988 | Friedman et al. |
| 4,776,853 A | 10/1988 | Klement et al. |
| 4,801,299 A | 1/1989 | Brendel et al. |
| 4,829,000 A | 5/1989 | Kleinman et al. |
| 4,902,508 A | 2/1990 | Badylak et al. |
| 4,912,057 A | 3/1990 | Guirguis et al. |
| 4,956,178 A | 9/1990 | Badylak et al. |
| 5,032,508 A | 7/1991 | Naughton et al. |
| 5,266,480 A | 11/1993 | Naughton et al. |
| 5,275,826 A | 1/1994 | Badylak et al. |
| 5,281,422 A | 1/1994 | Badylak et al. |
| 5,336,616 A | 8/1994 | Livesey et al. |
| 5,352,463 A | 10/1994 | Badylak et al. |
| 5,372,821 A | 12/1994 | Badylak et al. |
| 5,478,739 A | 12/1995 | Slivka et al. |
| 5,518,915 A | 5/1996 | Naughton et al. |
| 5,604,106 A | 2/1997 | Liotta et al. |
| 5,753,267 A | 5/1998 | Badylak et al. |
| 6,171,344 B1 | 1/2001 | Atala |
| 6,206,931 B1 | 3/2001 | Cook et al. |
| 6,485,723 B1 * | 11/2002 | Badylak et al. ............ 424/93.7 |

FOREIGN PATENT DOCUMENTS

| WO | WO 92/15676 | 9/1992 |
| WO | WO 93/00441 | 1/1993 |
| WO | WO 97/17038 | 5/1997 |

OTHER PUBLICATIONS

Boder G.B., Root M. A., Chance R.E., and Johnson I.S., *Long-Term Production of Insulin by Isolated Rabbit Pancreatic Islets in Suspension Culture.*, J. Cell Biol. 39:16a (1968).

Boder G.B., Root M., Chance R.E. Johnson, I.S., *Extended Production of Insulin by Isolated Rabbit Pancreatic Islets;Evidence for Biosynthesis of Insulin*, Proc. Soc. Exptl. Biol. Med., 131:507-513 (1969).

Boder G.B., Kleinschmidt W., Harley R.J., and Williams D.C. *Visible Light Inhibits Growth of Chinese Hamster Ovary Cells,.* European J. Cell Biol., 31:132-136 (1983).

Boder G.B., Shaw W.N. and Smith R.E., *Long Term Monolayer Cultures of Islet Cells from Neonatal Mice,.* J. Cell Biol. 59:29a (Nov. 1973).

Larsson L., Boder G.B. and Shaw W.N., *Changes in the Islets of Langerhans in the Obese Zucker Rat*, Lab. Invest. 36:593-598 (1977).

Williams D.C., Paul D.C., Johnston, Jr. C.C., and Boder G.B., *Mineralization in Cultured Adult Rat Bone Cells: Evaluation by Video Time Lapse, Scanning Electron Microscopy and Energy Dispersive X-ray Analyses*, J. Cell Biol. 91:22a, abstract No. 1031 (1981).

Boder G.B. and Hull R.H., *Introduction to Techniques in Mammalian Cell Culture*, Manual of Industrial Microbiology and Biotechnology, Ed. A.L. Demain and N.A. Solomon, p. 248-262 (1986).

Backer M.P., Metzger L.S., Slaber P.L., Nevitt K.L., and Boder G.B., *Large Scale Production of Monoclonal Antibodies in Suspension Culture*, Biotechnology and Bioengineering, 32:993-1000 (1988).

Girasole et al., *17-β Estradiol Inhibits IL-6 Production by Bone Marrow-Derived Stromal Cells and Osteoblasts In Vitro: A Potential Mechanism for the Antiosteoporotic Effects of Estrogens*, The Journal of Clinical Investigation, Inc., 89:883-891 (1992).

Boder, G.B., *Mammalian Cell Cultures for Genetically Engineered Products*, Toxicologic Pathology, vol. 17, No. 4, p. 827 (1989).

Badylak S.T., Boder G.B., Morff R., Lantz G., *Directed Connective Tissue Remodeling Upon a Biologic Collagen Substrate*, J. Cell Biochem. Supplement 16F, p. 124, abstract No. CE 027 (1992).

(Continued)

*Primary Examiner*—Leon B. Lankford, Jr.
*Assistant Examiner*—Susan Hanley
(74) *Attorney, Agent, or Firm*—Barnes & Thornburg LLP

(57) ABSTRACT

An improved tissue graft construct comprising submucosa of a warm-blooded vertebrate and a preselected group of eukaryotic cells are described. The improved tissue graft constructs can be used in accordance with the present invention to enhance the repair of damaged or diseased tissues in vivo.

16 Claims, No Drawings

OTHER PUBLICATIONS

Mikos A.G., Papadaki M.G., Kouvroukoglou S., Ishang S.L., and Thomson R.C., *Mini-Review: Islet Transplantation to Create a Bioartificial Pancreas*, Biotech. and Bioengineering, vol. 43, p. 673-677 (1994).

Kuo C.Y., Burghen G.A., Herrod H.G. and Budd T.W., *Tissue Engineering of Islet Gland Equivalent*, FASEB Journal, A302, abstract No. 1742 (1994).

Kuo C.Y., Burghen G.A., and Herrod H.G., *Biohybrid Islet-Gland Equivalent for Transplantation*, Journal of Cellular Biochemistry, Supplement 18C, PZ110, (Feb. 13-26, 1994).

Kleinman H.K., McGarvey M.L., Hassell J.R., Star V.L., Cannon F.B., Laurie G.W., and Martin G.R. *Basement Membrane Complexes with Biological Activity*, Biochemistry 25:312-318 (1986).

Kuo C.Y., Herrod H.G., and Burghen G.A., *Formation of Pseudoislets from Human Pancreatic Cultures*, Pancreas, vol. 7, No. 3, p. 320-325 (1992).

Freshney R.I., *Culture of Animal Cells: A Manual of Basic Technique*, Chapters 12 and 13, pp. 119-143. Alan R. Liss, Inc.,New York (1994).

*Bioartificial Organs*, Richard Skalak and Fred Fox, eds. Tissue Engineering, *Chapter V. Transplants and Artificial Organs*, pp. 209, 211-239, and 241-242 (Alan R. Liss, Inc. 1988).

Emerman et al., *Maintenance and Induction of Morphological Differentiation in Dissociated Mammary Epithelium on Floating Collagen Membranes*, In Vitro, vol. 13, No. 5, pp. 316-328 (1977).

Bell et al., *Production of a tissue-like structure by contraction of collagen lattices by human fibroblasts of different proliferative potential in vitro*, Proc. Natl. Sci. USA, vol. 76, No. 3, pp. 1274-1278 (Mar. 1979).

Elsdale & Bard, *Collagen Substrata for Studies on Cell Behavior*, The Journal of Cell Biology, vol. 54, pp. 626-637 (1972).

Kleinman et al., *Preparation of Collagen Substrates for Cell Attachment: Effect of Collagen Concentration and Phosphate Buffer*, Analytical Biochemistry, 94:308-312 (1979).

Vitrogen 100® Purified Collagen for Cell Culture and Biochemistry: Product Information Sheet, p. 1-2 (1980).

Grinnell, *Cell-Collagen Interactions: Overview*, Methods in Enzymology, 82:499-503 (1982).

Lee et al., *Modulation of Secreted Proteins of Mouse Mammary Epithelial Cells by the Collagenous Substrata*, The Journal of Cell Biology, 98:146-155 (1984).

Schor et al., *The Use of Three-Dimensional Collagen Gels for the Study of Tumour Cell Invasion In Vitro: Experimental Parameters Influencing Cell Migration Into the Gel Matrix*, Int. J. Cancer, 29:57-62 (1982).

Shields et al., *Invasion of Collagen Gels by Mouse Lymphoid Cells*, Immunology, 51:259-268 (1984).

Schor et al., *Effects of Culture Conditions on the Proliferation, Morphology and Migration of Bovine Aortic Endothelial Cells*, J. Cell Sci., vol. 62, pp. 267-285 (1983).

Michalopoulos & Pitot, *Primary Culture of Parenchymal Liver Cells on Collagen Membranes*, Experimental Cell Research, vol. 94, pp. 70-78 (1975).

Ibrahiem, E. I. H et al., *Orthotopic Implantation of Primary N-[4-(5-Nitro-2-furyl)-2-thiazolyl]formamide-induced Bladder Cancer in Bladder Submucosa: An Animal Model for Bladder Cancer Study*, Cancer Research, vol. 43:617-620 (Feb. 1983).

Kashtan, H. et al., *Intra-rectal injection of tumor cells: a novel animal model of rectal cancer*, Surgical Oncology, 1:251-256 (1992).

Sigma 1994 Catalogue and Price List, Plant Cell Culture Equipment, p. 160.

DeLuca et al., *Evidence that Human Oral Epithelium Reconstituted In Vitro and Transplanted onto Patients with Defects in the Oral Mucosa Retains Properties of the Original Donor Site*, Transplantation, vol. 50(3), pp. 454-459 (1990).

Freed et al., *Joint Resurfacing Using Allograft Chondrocytes and Synthetic Biodegradable Polymer Scaffolds*, J. Biomedical Materials Res., vol. 28, pp. 891-899 (1994).

Rudert & Wirth, Cartilage Cell Transplantation. Experimental Principles and Clinical Applications, Orthopade, vol. 26(8), p. 741-747 (abstract) (1997) available at http://www.ncbi.nlm.nih.gov/htbin-post/Entrez/.

Wakitani et al., *Mesenchymal Cell-Based Repair of Large, Full-Thickness Defects of Articular Cartilage*, J. Bone Joint Surg. Am., vol. 76(4), p. 579-592 (abstract) (1994) available at http://www.ncbi.nlm.nih.gov/htbin-post/Entrez/.

Blay et al., *Epidermal growth factor promotes the chemotactic migration of cultured rat intestinal epithelial cells*, J. Cell Physiology, 124(1):107-112 (1985).

Bruch et al., *Rekonstruktion der arteriellen Strombahn durch autologe intestinale Muskeltransplantate beim Hund*, Folia Angiologica, XXIX(3-5):65-68 (1981).

* cited by examiner

ENHANCED SUBMUCOSAL TISSUE GRAFT CONSTRUCTS

CROSS REFERENCE TO RELATED APPLICATIONS

This application is a divisional of U.S. application Ser. No. 09/566,497, filed on May 8, 2000, now U.S. Pat. No. 6,485,723, which is a continuation of U.S. application Ser. No. 09/151,790, filed on Sep. 11, 1998 now abandoned, which is a continuation-in-part of U.S. application Ser. No. 08/530,002, filed on Sep. 19, 1995, now U.S. Pat. No. 5,866,414, issued on Feb. 2, 1999, a divisional of U.S. application Ser. No. 08/386,452, filed on Feb. 10, 1995, now U.S. Pat. No. 5,695,998, issued on Dec. 9, 1997.

FIELD OF THE INVENTION

The present invention relates to intestinal tissue derived tissue grafts and their use in repairing damaged or diseased tissues. More particularly, this invention is directed to intestinal submucosal tissue grafts that have been seeded with a preselected population of cells to enhance the repair capabilities of the tissue graft construct.

BACKGROUND AND SUMMARY OF THE INVENTION

The present invention is directed to vertebrate submucosa-derived collagenous matrices in combination with preselected cell population as tissue graft construct for the use in the repair of damaged or diseased tissues. The collagenous matrices for use in accordance with the present invention comprise highly conserved collagens, glycoproteins, proteoglycans, and glycosaminoglycans in their natural configuration and natural concentration. The extracellular collagenous matrix for use in this invention is derived from submucosal tissue of a warm-blooded vertebrate.

In accordance with the present invention the submucosa is isolated from warm-blooded vertebrate tissues including the alimentary, respiratory, intestinal, urinary or genital tracts of warm-blooded vertebrates. The preparation of intestinal submucosa is described and claimed in U.S. Pat. No. 4,902,508, the disclosure of which is expressly incorporated herein by reference. Urinary bladder submucosa and its preparation is described in U.S. Pat. No. 5,554,389, the disclosure of which is expressly incorporated herein by reference. Stomach submucosa has also been obtained and characterized using similar tissue processing techniques. Such is described in U.S. patent application No. 60/032,683 titled STOMACH SUBMUCOSA DERIVED TISSUE GRAFT, filed on Dec. 10, 1996. Briefly, stomach submucosa is prepared from a segment of stomach in a procedure similar to the preparation of intestinal submucosa. A segment of stomach tissue is first subjected to abrasion using a longitudinal wiping motion to remove the outer layers (particularly the smooth muscle layers) and the luminal portions of the tunica mucosa layers. The resulting submucosa tissue has a thickness of about 100 to about 200 micrometers, and consists primarily (greater than 98%) of acellular, eosinophilic staining (H&E stain) extracellular matrix material.

Preferred submucosal tissues for use in accordance with this invention include intestinal submucosa, stomach submucosa, urinary bladder submucosa, and uterine submucosa. Intestinal submucosal tissue is one preferred starting material, and more particularly intestinal submucosa delaminated from both the tunica muscularis and at least the tunica mucosa of warm-blooded vertebrate intestine.

As a tissue graft, submucosal tissue undergoes remodeling and induces the growth of endogenous tissues upon implantation into a host. It has been used successfully in vascular grafts, urinary bladder and hernia repair, replacement and repair of tendons and ligaments, and dermal grafts. The preparation and use of submucosa as a tissue graft composition is described in U.S. Pat. Nos. 4,902,508; 5,281,422; 5,275,826; 5,554,389; and other related U.S. patents. When used in such applications the graft constructs appear not only to serve as a matrix for the regrowth of the tissues replaced by the graft constructs, but also promote or induce such regrowth of endogenous tissue. Common events to this remodeling process include: widespread and very rapid neovascularization, proliferation of granulation mesenchymal cells, biodegradation/resorption of implanted intestinal submucosal tissue material, and lack of immune rejection. The use of submucosal tissue in sheet form and fluidized forms for inducing the formation of endogenous tissues is described and claimed in U.S. Pat. Nos. 5,281,422 and 5,275,826, the disclosures of which are expressly incorporated herein by reference.

Submucosal tissue can be obtained from various sources, including intestinal tissue harvested from animals raised for meat production, including, for example, pigs, cattle and sheep or other warm-blooded vertebrates. This tissue can be used in either its natural configuration or in a comminuted or partially digested fluidized form. Vertebrate submucosal tissue is a plentiful by-product of commercial meat production operations and is thus a low cost cell growth substrate, especially when the submucosal tissue is used in its native layer sheet configuration.

The submucosa tissue graft constructs prepared in accordance with the present invention are a substantially acellular matrix that provides a superior cell growth substrate resembling the matrix environment found in vivo. The natural composition and configuration of submucosal tissue provides a unique cell growth substrate that promotes the attachment and proliferation of cells.

It has been reported that compositions comprising submucosal tissue of the intestine of warm-blooded vertebrates can be used as tissue graft materials in sheet or fluidized form. U.S. Pat. No. 4,902,508 describes tissue graft compositions that are characterized by excellent mechanical properties, including high compliance, a high burst pressure point, and an effective porosity index. These properties allow such compositions to be used for vascular and connective tissue graft constructs. When used in such applications the preferred graft constructs serve as a matrix for the in vivo regrowth of the tissues replaced by the graft constructs. U.S. Pat. No. 5,275,826 describes use of fluidized forms of vertebrate submucosal tissues as injectable or implantable tissue grafts.

The present invention is directed to submucosa tissue graft constructs and a method of enhancing or expanding the functional properties of vertebrate submucosal tissues as an implantable or injectable tissue graft construct. The improved tissue graft constructs are prepared by seeding the submucosal tissue in vitro with preselected or predetermined cell types prior to implanting or injecting the graft construct into the host.

DETAILED DESCRIPTION OF THE PREFERRED EMBODIMENTS

The present invention is directed to an improved tissue graft construct comprising vertebrate submucosa delaminated from both the external smooth muscle layers and the luminal portions of the tunica mucosa. The improvement comprises the addition of a preselected population of cells to the substantially acellular submucosa matrix. The cells to be combined with the submucosa are selected based on the cell type of the intended tissue to be repaired. In one embodiment the preselected cells comprise primary cells isolated from epithelial, endothethial or cartilage tissues.

There are certain areas of the body that contain a combination of complex differentiated structures for which regeneration has never shown to be possible. These areas typically heal with great difficulty and damage to these structures creates significant morbidity and often mortality. Examples of such areas include the esophagus, the central nervous system, skin and its appendages, among others.

The combination of the preselected population of cells with the submucosa matrix provides an improved tissue graft construct that shows surprising improved wound healing capabilities and better restoration of tissue function when compared to the use of either component alone as a therapeutic agent. Furthermore, the composition comprising submucosa seeded with added cells can be cultured prior to the implantation of the construct into the affected region. Intestinal submucosa is capable of supporting the proliferation and growth of a wide variety of cells, including primary cells that are normally difficult to culture in vitro. The ability of submucosa to provide a substrate that supports the growth of such cells provides the opportunity to expand a population of cells prior to implantation into a host. In one embodiment the submucosa is seeded with autologenous cells isolated from the patient to be treated.

There is provided in accordance with this invention a method and composition for supporting the proliferation and inducing tissue differentiation of eukaryotic cells cultured in vitro. Generally the method comprises the step of contacting eukaryotic cells, in vitro, with a vertebrate submucosa-derived collagenous matrix under conditions conducive to eukaryotic cell growth. The term "contacting" as used herein with reference to cell culture is intended to include both direct and indirect contact, for example in fluid communication, of the submucosal tissue and the cultured cells. The term "conditions conducive to eukaryotic cell growth" as used herein refers to the environmental conditions, such as sterile technique, temperature and nutrient supply, that are considered optimal for eukaryotic cell growth under currently available cell culture procedures. Although optimum cell culture conditions used for culturing eukaryotic cells depend somewhat on the particular cell type, cell growth conditions are generally well known in the art. However a number of differentiated cell types are still considered difficult to culture (i.e. islets of Langerhans, hepatocytes, chondrocytes, osteoblasts, etc.).

The collagenous matrix component of the present cell culture substrate is derived from vertebrate submucosa and comprises naturally associated extracellular matrix proteins, glycoproteins and other factors. Preferably the collagenous matrix comprises intestinal submucosal tissue of a warm-blooded vertebrate. The small intestine of warm-blooded vertebrates is a particularly preferred source of the cell culture substrate for use in this invention.

Suitable intestinal submucosal tissue typically comprises the tunica submucosa delaminated from the tunica muscularis and at least the luminal portion of the tunica mucosa. In one preferred embodiment of the present invention the intestinal submucosal tissue comprises the tunica submucosa and basilar portions of the tunica mucosa including the lamina muscularis mucosa and the stratum compactum which layers are known to vary in thickness and in definition dependent on the source vertebrate species.

The preparation of submucosal tissue for use in accordance with this invention is described in U.S. Pat. No. 4,902,508, the disclosure of which is expressly incorporated herein by reference. A segment of vertebrate intestine, preferably harvested from porcine, ovine or bovine species, but not excluding other species, is subjected to abrasion using a longitudinal wiping motion to remove the outer layers, comprising smooth muscle tissues, and the innermost layer, i.e., the luminal portion of the tunica mucosa. The submucosal tissue is rinsed with saline and optionally sterilized; it can be stored in a hydrated or dehydrated state. Lyophilized or air dried submucosa tissue can be rehydrated and used in accordance with this invention without significant loss of its cell proliferative activity.

The submucosa component of the present invention can be sterilized, prior to the addition of the preselected cells, using conventional sterilization techniques including glutaraldehyde tanning, formaldehyde tanning at acidic pH, propylene oxide treatment, gas plasma sterilization, gamma radiation, electron beam, peracetic acid sterilization. Sterilization techniques which do not adversely affect the mechanical strength, structure, and biotropic properties of the submucosal tissue is preferred. For instance, strong gamma radiation may cause loss of strength of the sheets of submucosal tissue. Preferred sterilization techniques include exposing the graft to peracetic acid, 1–4 Mrads gamma irradiation (more preferably 1–2.5 Mrads of gamma irradiation) or gas plasma sterilization; peracetic acid sterilization is the most preferred sterilization method. Typically, the submucosal tissue is subjected to two or more sterilization processes. After the submucosal tissue is sterilized, for example by chemical treatment, the tissue may be wrapped in a plastic or foil wrap and sterilized again using electron beam or gamma irradiation sterilization techniques.

The submucosal tissue specified for use in accordance with this invention can also be in a fluidized form. Submucosal tissue can be fluidized by comminuting the tissue and optionally subjecting it to protease digestion to form a homogenous solution. The preparation of fluidized forms of submucosa tissue is described in U.S. Pat. No. 5,275,826, the disclosure of which is expressly incorporated herein by reference. Fluidized forms of submucosal tissue are prepared by comminuting submucosa tissue by tearing, cutting, grinding, or shearing the harvested submucosal tissue. Thus pieces of submucosal tissue can be comminuted by shearing in a high speed blender, or by grinding the submucosa in a frozen or freeze-dried state to produce a powder that can thereafter be hydrated with water or a buffered saline to form a submucosal fluid of liquid, gel or paste-like consistency. The fluidized submucosa formulation can further be treated with a protease such as trypsin or pepsin at an acidic pH for a period of time sufficient to solubilize all or a major portion of the submucosal tissue components and optionally filtered to provide a homogenous solution of partially solubilized submucosa.

The viscosity of fluidized submucosa for use in accordance with this invention can be manipulated by controlling the concentration of the submucosa component and the degree of hydration. The viscosity can be adjusted to a range of about 2 to about 300,000 cps at 25° C. Higher viscosity formulations, for example, gels, can be prepared from the submucosa digest solutions by adjusting the pH of such solutions to about 6.0 to about 7.0.

Applicants have discovered that compositions comprising submucosal tissue can be used for supporting growth or proliferation of eukaryotic cells in vitro. Submucosal tissue can be used in accordance with this invention as a cell growth substrate in a variety of forms, including its native sheet-like configuration, as a gel matrix, as an addition for art-recognized cell/tissue culture media, or as coating for culture-ware to provide a more physiologically relevant substrate that supports and enhances the proliferation of cells in contact with the submucosal matrix. The submucosal tissue provides surfaces for cell adhesion and also induces cell differentiation. The submucosal tissue is preferably sterilized prior to use in cell culture applications, however nonsterile submucosal tissue can be used if antibiotics are included in the cell culture system.

In one preferred embodiment cells are seeded directly onto sheets of vertebrate submucosal tissue under conditions conducive to eukaryotic cell proliferation. The porous nature of submucosal tissue allows diffusion of cell nutrients throughout the submucosal matrix. Thus, for example, cells can be cultured on either the luminal or abluminal surface of the submucosal tissue. The luminal surface is the submucosal surface facing the lumen of the organ source and typically adjacent to an inner mucosa layer in vivo whereas the abluminal surface is the submucosal surface facing away from the lumen of the organ and typically in contact with smooth muscle tissue in vivo.

Cells cultured on solid sheets of vertebrate submucosal tissue display a different growth pattern, and exhibit different interactions with the submucosal growth substrate, depending on which side of the submucosal sheet the cells are grown. Histological examination of tissue/cells cultured on intestinal submucosal tissue sheets in accordance with this invention reveals that cells that are seeded onto the abluminal surface not only grow/proliferate along the surface of the submucosal tissue, but they also more readily migrate into and proliferate within the submucosal tissue itself. The luminal surface comprises a more dense matrix than the abluminal side and thus cells are less likely to penetrate the luminal side. Cells that are seeded onto the luminal surface attach to the matrix but generally do not penetrate the surface. However certain cell types are capable of penetrating both the abluminal and luminal surfaces (eg squamous carcinoma cells and fibroblasts). In addition, certain cell types, such as fetal rat cells, when seeded on the luminal side proliferate to form a polylayer of cells. Cells of this polylayer can differentiate to perform functions characteristic of cells in vivo and indicative of their position in the polylayer.

In one embodiment of the present invention, cell growth substrates in accordance with the present invention are formed from fluidized forms of submucosal tissue. The fluidized submucosal tissue can be gelled to form a solid or semi-solid matrix. Eukaryotic cells can then be seeded directly on the surface of the matrix and cultured under conditions conducive to eukaryotic cell proliferation.

The cell growth substrate of the present invention can be combined with nutrients, including minerals, amino acids, sugars, peptides, proteins, or glycoproteins that facilitate cellular proliferation, such as laminin and fibronectin and growth factors such as epidermal growth factor, platelet-derived growth factor, transforming growth factor beta, or fibroblast growth factor. In one preferred embodiment fluidized or powder forms of submucosal tissue can be used to supplement standard eukaryotic culture media to enhance the standard media's capacity for sustaining and inducing the proliferation of cells cultured in vitro.

In accordance with the present invention there is provided a cell culture composition for supporting growth in vitro of an eukaryotic cell population in combination with submucosal tissue of a warm-blooded vertebrate. The composition comprises nutrients, and optionally growth factors required for optimal growth of the cultured cells. The submucosa substrates of the present invention can be used with commercially available cell culture liquid media (both serum based and serum free). When grown in accordance with this invention, proliferating cells can either be in direct contact with the submucosal tissue or they can simply be in fluid communication with the submucosal tissue. It is anticipated that the cell growth compositions of the present invention can be used to stimulate proliferation of undifferentiated stems cells as well as differentiated cells such as islets of Langerhans, hepatocytes and chondrocytes. Furthermore the described cell growth composition is believed to support the growth of differentiated cells while maintaining the differentiated state of such cells.

It has been well documented that submucosal tissue is capable of inducing host tissue proliferation, remodeling and regeneration of appropriate tissue structures upon implantation in a number of microenvironments in vivo (e.g., tendon, ligament, bone, articular cartilage, artery, and vein). The use of such tissue in sheet form and fluidized forms for inducing the formation of endogenous tissues is described and claimed in U.S. Pat. Nos. 5,281,422 and 5,275,826, the disclosures of which are expressly incorporated by reference.

In one embodiment of the present invention the tissue replacement capabilities of graft compositions comprising submucosal tissue of warm-blooded vertebrates are further enhanced or expanded by seeding the tissue with various cell types, prior to implantation. For example, submucosal tissue may be seeded with endothelial cells or keratinocytes and used as a vascular graft or skin replacement, respectively. In one embodiment the submucosal tissue is seeded with islet of langerhans cells for use as an auxiliary pancreas. Alternatively, the submucosal tissue can be seeded with mesenchymal cells (stem cells) initially for expansion of the cell population and thereafter for implantation into a host. Submucosal tissue can also serve as a delivery vehicle for introducing genetically modified cells to a specific location in a host. The submucosal tissue for use in accordance with this embodiment can either be in a fluidized form or in its native solid form. Optionally, after the submucosal tissue has been seeded with eukaryotic cells, the graft composition can be subjected to conditions conducive to the proliferation of eukaryotic cells to further expand the population of the seeded cells prior to implantation of the graft into the host.

In one embodiment, compositions comprising submucosal tissue and a proliferating cell population can be encapsulated in a biocompatible matrix for implantation into a host. The encapsulating matrix can be configured to allow the diffusion of nutrients to the encapsulated cells while allowing the products of the encapsulated cells to diffuse from the encapsulated cells to the host cells. Suitable biocompatible polymers for encapsulating living cells are known to those skilled in the art. For example a polylysine/alginate encapsulation process has been previously described by F. Lim and A. Sun (Science Vol. 210 pp. 908–910). Indeed, vertebrate submucosa itself could be used advantageously to encapsulate a proliferating cell population on a submucosal matrix in accordance with this invention for implantation as an artificial organ.

Submucosal tissue advantageously provides a physiological environment that supports the differentiation of cells cultured in vitro on the submucosal tissue. Thus, cell culture substrates comprising submucosal tissue can be used in combination with standard cell culture techniques known to those of ordinary skill in the art, to produce tissue grafts, in vitro, for implantation into a host in need thereof. The cells of such a tissue perform their proper natural function based on cell type and position within the submucosal tissue graft construct.

The method of forming a tissue graft in vitro comprises the steps of seeding eukaryotic cells onto a cell growth substrate comprising submucosal tissue of a warm-blooded vertebrate and culturing the cells in vitro under conditions conducive to proliferation of the eukaryotic cells. Advantageously the synthesis in vitro of a tissue graft construct, wherein the cells of the tissue perform their proper natural function, allows the generation of tissue grafts from an initially small cell population that can be expanded in vitro prior to implantation.

In accordance with one embodiment of the present invention an improved tissue graft construct is provided. The tissue graft construct comprises tunica submucosa delaminated from both the tunica muscularis and at least the luminal portion of the tunica mucosa of vertebrate intestinal tissue combined with a preselected population of cells. In one embodiment the preselected population of cells includes connective tissue precursor cells. Intestinal submucosa can induce the differentiation of precursor cells into cells that assist in the repair of damaged tissues. Advantageously, submucosa seeded with a population of precursor cells can be implanted into a variety of different in vivo locations and the precursor cells will differentiate into the appropriate cell type for the environment. For example, implantation of the composition adjacent to cartilage or bone will result in the graft construct remodeling into cartilage or bone.

In accordance with one embodiment vertebrate submucosa is combined with primary cells to form an improved vertebrate submucosa tissue graft construct. In one embodiment, the improved tissue graft construct comprises vertebrate submucosa delaminated from both the external smooth muscle layers and the luminal portions of the tunica mucosa and added primary cells. More particularly, in one embodiment the vertebrate submucosa comprises tunica submucosa delaminated from both the tunica muscularis and at least the luminal portion of the tunica mucosa of vertebrate intestinal tissue. The improved graft construct of the present invention are implanted into an in vivo site in need of repair to enhance the repair of the endogenous tissues. The primary cells can be selected from the group consisting of endothelial, keratinocytes, chondrocytes, epithelial and mesenchymal cells. Typically, the submucosa will be in a solid form, however in an alternative embodiment the submucosa utilized is fluidized submucosa. The submucosa can be fluidized by comminuting the tissue and/or digesting the submucosa with an enzyme for a period of time sufficient to solubilize the submucosa.

In one embodiment, the improved tissue graft construct of the present invention comprises tunica submucosa delaminated from both the tunica muscularis and at least the luminal portion of the tunica mucosa of vertebrate intestinal tissue and a population of primary cells selected from the group consisting of endothelial cells, keratinocytes and mesenchymal cells. Furthermore, the preselected cell type may include cells that have been genetically modified. For example, the cell may be modified by including genes that express proteins that enhance the repair of the damaged or diseased tissues.

The present invention further provides a method for enhancing the capabilities of a submucosa graft construct to repair articular cartilage defects. The method comprises the step of seeding the vertebrate submucosa with chondrocytes prior to implanting or injecting the graft construct into a host. Accordingly, in one embodiment of the present invention a composition for the repair of articular cartilage defects comprises tunica submucosa delaminated from both the tunica muscularis and at least the luminal portion of the tunica mucosa of vertebrate intestinal tissue and added primary chondrocyte cells.

The present invention also provides a method for enhancing the capabilities of vertebrate submucosa graft construct to repair epithelial defects (such as periodontal structures or the esophagus), said method comprising the step of seeding the submucosa with primary epithelial cells prior to implanting or injecting the graft construct into a host. The method of repairing these tissue can further comprising the step of subjecting the seeded graft construct to conditions conducive to the proliferation of the cells prior to implanting or injecting the graft material into the host.

Accordingly, in one embodiment of the present invention a composition for the repair of periodontal structures or the, esophagus comprises tunica submucosa delaminated from both the tunica muscularis and at least the luminal portion of the tunica mucosa of vertebrate intestinal tissue and added primary epithelial cells, and more particularly primary epithelial cells selected from the group consisting of primary gingiva epithelial cells and primary esophageal epithelial cells.

EXAMPLE 1

Sterilization of Submucosal Tissue

Because cell culture techniques must be performed under strict aseptic conditions, if antibiotics are not included in the culture system, the submucosa tissue must be prepared in a sterile manner for use as a cell culture substrate. Numerous sterilization methods have been investigated to assess the effect of sterilization on the biotropic properties of submucosal tissue. Sterilization techniques which do not significantly weaken the mechanical strength and biotropic properties of the tissue are preferred. The following sterilization methods for intestinal submucosa have been evaluated: peracetic acid sterilization, 2.5 Mrad gamma-irradiation, 1.0 Mrad gamma-irradiation, Exspor (Alcide, Norfolk, Conn.) sterilization and various combinations of these sterilization methods. Gamma-irradiation was performed on hydrated submucosal tissue using a $^{60}$Cobalt-gamma chamber. Exspor sterilization was performed according to manufacturer's specifications using a sterilant volume (ml) to intestinal submucosa (g) ratio of 10 to 1.

Various cell types (e.g., IMR-90, FR, HT-29, RPEC) were seeded upon the sterilized submucosa and their growth characteristics were analyzed at 1,3,7 and 14 days. Results obtained for all cell types showed that submucosal derived growth substrates sterilized by gamma irradiation or peracetic acid treatments supported some degree of adherence and growth of cells. However, cells seeded onto peracetic acid sterilized submucosal derived substrates showed increased adherence, increased survival, and enhanced rates of proliferation and differentiation; peracetic acid appears to be the preferred sterilization technique for preparation of submucosa as a cell culture substrate.

EXAMPLE 2

Sterilization of Submucosal Tissue with Peracetic Acid

Submucosal tissue is soaked in a peracetic acid/ethanol solution for 2 hours at room temperature using a ratio of 10:1 (mls peracetic solution: grams submucosal tissue) or greater. The peracetic acid/ethanol solution comprises 4% ethanol, 0.1% (volume: volume) peracetic acid and the remainder water. The 0.1% peracetic acid component is a dilution of a 35% peracetic acid stock solution commercially available and defined as in table 1. Preferably, the submucosal tissue is shaken on a rotator while soaking in the peracetic acid solution. After two hours, the peracetic acid solution is poured off and replaced with an equivalent amount of lactated Ringer's solution or phosphate buffered saline (PBS) and soaked (with shaking) for 15 minutes. The submucosal tissue is subjected to four more cycles of washing with lactated Ringer's or PBS and then rinsed with sterile water for an additional 15 minutes.

TABLE 1

Chemical Composition of the 35% Peracetic Acid Solution

| Composition, % by weight | |
| --- | --- |
| Peracetic acid | 35.5 |
| Hydrogen peroxide | 6.8 |
| Acetic acid | 39.3 |
| Sulfuric acid | 120 |
| Water | 17.4 |
| Acetyl peroxide | 0.0 |
| Stabilizer | 500 PPM |
| Typical active oxygen analysis, % by weight | |
| Active Oxygen as peracid | 7.47 |
| Active Oxygen as $H_2O_2$ | 2.40 |
| Total active oxygen | 10.67 |

In order to promote a further understanding of the present invention and its features and advantages, the following specific Examples are provided. It will be understood that these specific Examples are illustrative, and not limiting, of the present invention.

EXAMPLE 3

Growth Characteristics of Various Cell Types on Sterilized Submucosa

Small intestinal submucosa was harvested and prepared from freshly euthanatized pigs as described in U.S. Pat. No. 4,902,508. Following sterilization via various techniques (gamma irradiation, peracetic acid, etc.), the submucosal tissue was clamped within a polypropylene frame to create a flat surface area (50 $mm^2$) for cell growth. The frame was submerged in culture medium to allow access of medium nutrients to both surfaces of the submucosal tissue. Various cell types were seeded ($3 \times 10^4$ cells/submucosal tissue section) on the submucosal tissue and then placed in a 5% $CO_2$, 95% air incubator at 37° C. Following various periods of time, the seeded submucosal tissue was fixed in 10% neutral buffered formalin, embedded in paraffin, and sectioned (6 um). Various histological and immunohistochemical staining procedures were then applied to determine the cell growth characteristics.

To date, the growth characteristics of the following cell lines have been studied using submucosal tissue as a growth substrate:

| CELL LINE | CELL LINE DESCRIPTION |
| --- | --- |
| CHO | Chinese hamster ovary cells |
| 3T3 | Swiss albino mouse embryo fibroblasts |
| C3H10T½ | C3H mouse embryo, multi-potential |
| FR | Fetal rat skin (Sprague Dawley) |
| IMR90 | Human fetal lung fibroblasts |
| HT-29 | Human colon adenocarcinoma, moderately well differentiated, grade II |
| RPEC | Rat pulmonary endothelial cells |
| HUVEC | Human umbilical vein cells |
| SCC-12 | Squamous Cell Carcinoma |

Table 2 summarizes various cell types and the corresponding specific medium conditions used to culture on the submucosa derived cell culture substrates. The medium chosen represents optimal or near optimal conditions for propagation of each cell type under standard cell culture conditions (i.e., plastic tissue culture flasks). All cell preparations were incubated at 37° C. in a humidified atmosphere of 5% $CO_2$/air.

TABLE 2

Cell types and corresponding culture conditions investigated using Intestinal Submucosal Tissue as a cell growth matrix

| CELL TYPE | MEDIUM |
| --- | --- |
| 3T3 (American Type Culture Collection (ATCC), CRL 1658) Swiss mouse embryo fibroblasts | DMEM (Dulbecco's modified Eagle's medium) with 1.5 g/L $NaHCO_3$, 10% NNCS (neonatal calf serum), 100 U/ml penicillin, 100 ug/ml streptomycin, 2 mM L-glutamine |
| FR (ATCC, CRL 1213) cell line developed from a skin biopsy of a fetal (18 day gestation) germ-free Sprague Dawley rate | DMEM, 10% NNCS, 100 U/ml penicillin, 100 ug/ml streptomycin, 2 mM L-glutamine |
| HT-29 (ATCC, HTB 38) cell line derived from human colon adenocarcinoma | McCoy's, 10% NNCS, 100 U/ml penicillin, 100 ug/ml streptomycin, 2 mM L-glutamine |
| HUV-EC-C (ATCC, CRL 1730) endothelial cell line isolated from human umbilical vein | F12 K medium, 10% FBS (fetal bovine serum), 100 ug/ml heparin, 50 ug/ml endothelial cell growth supplement, 100 U/ml penicillin, 100 ug/ml streptomycin, 2 mM L-glutamine |

TABLE 2-continued

Cell types and corresponding culture conditions investigated using Intestinal Submucosal Tissue as a cell growth matrix

| CELL TYPE | MEDIUM |
|---|---|
| IMR-90 (ATCC, CCL 186) human diploid fibroblasts | McCoy's 5A medium, 20% NNCS, 100 U/ml penicillin, 100 ug/ml streptomycin, 2 mM L-glutamine |
| RPEC (J. P. Robinson, Purdue University) endothelial cell line derived from rat pulmonary endothelial cells | RPMI 1640, 5% NCS (newborn calf serum) 5% FBS (fetal bovine serum), 100 U/ml penicillin, 100 ug/ml streptomycin, 2 mM L-glutamine |
| C3H10T½ (ATCC, CCL 226) mouse embryo fibroblasts | BME (basal medium Eagle), 10% FBS, 100 U/ml penicillin, 100 ug/ml streptomycin, 2 mM L-glutamin |
| SCC-12 (W. Greenlee, Purdue University) squamous cell carcinoma | DMEM, 5% FBS (fetal bovine serum), 4 mM L-glutamine, 1 mM sodium pyruvate |
| CHO (Chinese Hamster Ovary Cells) | F12 Medium 10% FBS with antibiotics (Neomycm) |

The cellular growth on both the luminal and abluminal sides of intestinal submucosal tissue has been investigated. Intestinal submucosal tissue as a growth substrate exhibits sidedness; that is, the cell/matrix interactions are different when the cells are cultured on the abluminal versus the luminal side of the intestinal submucosal tissue. When selected cell types, such as rat FR cells are seeded on the luminal side, the cells attach to the matrix surface and proliferate to form a cellular polylayer. Alternatively, when FR cells are seeded on the abluminal side, the cells not only grow along the surface but also migrate into the submucosal matrix.

The stratum compactum of the luminal side of vertebrate intestinal submucosal tissue provides a dense connective tissue matrix and more readily supports monolayer or polylayer formation of select cell types (i.e. endothelial and epithelial cells). Alternatively, the abluminal side represents a more loose connective tissue structure that more readily supports migration of cells within the matrix structure (i.e. fibroblasts).

IMR-90 fibroblasts, when seeded upon the abluminal or luminal sides of the intestinal submucosal tissue, quickly became adherent and proliferated throughout the matrix components. These cells illustrated their characteristic spindle shape and large vesicular nucleus within the extracellular matrix components. However, 3T3 fibroblasts showed minimal adherence and growth potential when seeded upon the intestinal submucosal tissue.

Endothelial cells formed a confluent monolayer of spindle-shaped cells along the stratum compactum surface of the intestinal submucosal tissue within 3 days. At later times the monolayer became more dense and some cells intercalated down into the matrix components. Interestingly, some endothelial cells that penetrated into the matrix components formed a lining along the lumen of structures representing original blood vessels of the native intestine.

To date, the growth characteristics of the following primary cell strains have been studied using intestinal submucosal tissue as a growth substrate:

CELL STRAIN

Rat Cardiac Muscle
Porcine Smooth Muscle (aorta)
Porcine Endothelial (aorta)
Rabbit Smooth Muscle (aorta)
Rabbit Endothelial(aorta)
Porcine Smooth Muscle and Endothelial (mixed & co-cultured)
Human Osteoblasts Human Endothelial Cells Primary cell strains are cells that have been harvested from an organism and placed in culture. Subsequent passages of these cells (from 2–3 times) using standard in vitro cell culture techniques (to increase the number of cells) were frozen for later use. Each of the above listed cell strains was thawed, cultured in the presence of intestinal submucosal tissue and examined histologically. Each of the cultured cell strain populations proliferated and retained their differentiated appearance as determined by histological examination. For example, after 7–14 days of culture on intestinal submucosal tissue: the human osteoblast cells continued to accumulate appatite crystals and respond to osteogenic stimuli such as hormones; rat cardiac muscle cells retained their contractile properties; porcine smooth muscle cells retained smooth muscle actin; and porcine endothelial cells made factor eight.

EXAMPLE 4

Intestinal Submucosal Cell Culture Substrates as a Tumor Cell Growth Model System The morphology and invasive properties of an established cell line from a human squamous cell carcinoma of the face known as SCC-12 (obtained from W. Greenlee, Purdue University) cultured in vitro were studied. When grown under standard cell culture conditions for skin cells (e.g., gamma-irradiated or mitomycin C-treated feeder layer of Swiss 3T3 mouse fibroblasts) a monolayer of flattened cells is formed. However SCC-12 cells when seeded upon the abluminal surface of intestinal submucosal tissue, showed, upon histological examination active degradation of the submucosal matrix components and invasion of the intestinal submucosal tissue.

SCC-12 cells were seeded ($3 \times 10^4$ cells/0.8 cm$^2$ of intestinal submucosal tissue) on either the abluminal or luminal surface of sterilized intestinal submucosal tissue and floated in growth medium consisting of DMEM containing 5% fetal calf serum, 4 mM L-glutamine, and 1 mM sodium pyruvate. At timepoints representing 3, 7, 14, and 21 days, the growth characteristics were analyzed using standard histologic techniques. On day 3, the cells were strongly adherent and appeared to form a continuous layer (1–2 cells thick) along surface of the intestinal submucosal tissue. Morphologically, the cells were round and actively producing extracellular matrix products. After 7 days, a significant difference was noted in the cells' ability to invade the abluminal versus the luminal surface of the intestinal submucosal tissue. The layer of cells along the luminal surface of the intestinal submucosal tissue appeared to only increase in density. Alternatively, those cells seeded upon the abluminal surface, showed active degradation of the submucosal matrix components and penetration up to 30 um. At longer durations, there was an increasing number of cells at greater depths of penetration and a greater extent of intestinal submucosal tissue degradation. Although the SCC-12 cells actively invade intestinal submucosal tissue from both the abluminal and luminal surfaces, the observed invasion rate was greater when SCC-12 cells were placed on the abluminal side.

EXAMPLE 5

Intestinal Submucosal Tissue Supports Cytodifferentiation

FR Epithelial cells form a stratified polylayer when cultured on the luminal (stratum compactum) side of intestinal submucosal tissue. Cells adjacent to the intestinal submucosal tissue were columnar in shape and became progressively more flattened near the surface of the polylayer. After 14 days, structures resembling desmosomes were identified and the cellular layer stained positively for cytokeratin with a pan cytokeratin antibody. In addition, it appeared that the epithelial cells produced supporting matrix products (potentially basement membrane) as they do in vivo under normal healthy conditions. These findings suggest that the intestinal submucosal tissue supports natural epithelial cell maturation and differentiation processes.

The observed stratification of FR cells grown on the luminal side (stratum compactum) of a submucosal growth substrate provides evidence that the intestinal submucosal tissue supports and induces cellular differentiation in vitro. To verify the induction of cytodifferentiation of the FR cells, immunohistochemical and immunofluorescence analyses were performed for detecting the production of cytokeratin by FR cells cultured in the presence and absence of intestinal submucosal tissue. Cytokeratin is a predominant intracellular structural protein produced by terminally differentiated epithelial cells known as keratinocytes. Immunohistochemistry was performed on the protease-digested, formalin-fixed, paraffin embedded sections of FR cells grown on intestinal submucosal tissue using an anti-pan cytokeratin (C2931, Sigma, St. Louis, Mo.) as the primary antibody. Immunodetection was performed using the avidin-biotin complex (ABC) method and the Biogenex supersensitive StriAviGen kit (Vector Laboratories, Burlingame, Calif.). Tissue sections representing rat skin biopsies and HT29 cells grown on intestinal submucosal tissue were included in the analysis as positive and negative controls, respectively.

Results indicated a gradation of cytokeratin staining along the FR cellular polylayer with those cells at the surface of the polylayer staining most intensely. A similar positive staining pattern was observed in the cells forming the epidermal layer of the rat skin. However, no cytokeratin was detected in the specimens representing HT29 cells cultured on intestinal submucosal tissue.

An immunofluorescence analysis for cytokeratin was performed using flow cytometry to determine if the FR cell line expressed the differentiation product cytokeratin under standard culture conditions (in the absence of intestinal submucosal tissue). Swiss 3T3 Fibroblast (3T3) and squamous cell carcinoma (SCC-12) cell lines were included in the analysis as negative and positive controls respectively. Cells were harvested from tissue culture flasks, permeabilized using a cold methanol pretreatment, and incubated in the presences of anti-pan cytokeratin antibody at various dilutions (including the absence of anti-pan cytokeritin antibody to serve as a control). A goat anti-mouse antibody conjugated with fluorescein isothiocyanate (GAM-FITC) was then applied to facilitate immunodetection. The cell preparations were then analyzed on a EPICS Elite flow cytometer (Coulter Corp., Hialeah, Fla.) using 488 nm excitation produced by an air-cooled argon laser. Fluorescence emissions were measured at 525 nm with a bandpass filter. Untreated cells and cells treated only with GAM-FITC were also analyzed to establish background fluorescence levels. Table 3 represents the relative percentage of FITC fluorescence for each cell type following indirect immunofluorescence staining. As the data indicate only the positive control SCC-12 cell line expresses cytokeratin and the FR cell line does not express cytokeratin under standard culture conditions in the absence of submucosal substrate.

TABLE 3

Indirect Immunofluorescence Analysis for Cytokeratin SCC-12, 3T3 and FR Cells

| Cell Type | Dilution of Anti-Pan Cytokeratin | Percent GAM-FITC Fluorescence |
|---|---|---|
| SCC-12 | 0 (control) | 2% |
| SCC-12 | 1:100 | 72% |
| SCC-12 | 1:400 | 74% |
| SCC-12 | 1:1000 | 76% |
| SCC-12 | 1:4000 | 72% |
| 3T3 | 0 (control) | 11% |
| 3T3 | 1:100 | 10% |
| 3T3 | 1:400 | 18% |
| 3T3 | 1:1000 | 8% |
| 3T3 | 1:4000 | 5% |
| FR | 0 (control) | 6% |
| FR | 1:100 | 11% |
| FR | 1:400 | 6% |
| FR | 1:1000 | 4% |
| FR | 1:4000 | 4% |

EXAMPLE 6

Isolation of Hamster Pancreatic Islets

Hamster pancreatic islets were isolated as previously described by Gotoh et al. (*Transportation* Vol. 43, pp. 725–730(1987)). Briefly, 6–8 week old Golden hamsters (Harlan, Indianapolis, Ind.) were anesthetized via inhalation of Metofane (Methoxyflurane; Pitman-Moore; Mundelein, Ill.). The common bile duct was cannulated under a stereomicroscope with a polyethylene catheter (PE-10 tubing; CMS; Houston, Tex.), through which approximately 3–4 mls of ice cold M-199 medium (commercially available from Gibco BRL) containing 0.7 mg/ml of collagenase P was injected slowly until whole pancreas was swollen. The pancreas was excised and digested at 37° C. for approximately 50 minutes in M-199 medium containing 100 µg/ml of penicillin G and 100 µg/ml of streptomycin (no additional collagenase). The digest was washed three times in ice cold M-199 medium and passed sequentially through a sterile 500 µm stainless steel mesh, then a 100 µm mesh. Following purification by centrifugation through a ficoll density gradient (1.045, 1.075, 1.085 and 1.100) at 800 g for 10 min, islets were recovered from the top two interfaces.

Culturing of Pancreatic Islet Cells on Intestinal

Submucosal Tissue

Islets of Langerhans (islet cells) were cultured on submucosal cell growth substrates at 37° C. in an incubator supplemented with 5% CO and 95% air. The islet cells were cultured in the presence of various forms of intestinal submucosal tissue using the following procedures:
 1. Direct Contact: Intestinal submucosal tissue and the cultured cells physically contact one another.
 2. Indirect Contact: Intestinal submucosal tissue and the cultured cells are separated by a stainless steel mesh.
 3. Solubilized intestinal submucosal tissue is added to the culture media
 4. Cells are cultured on solubilized intestinal submucosa coated culture plate. The coating was applied by placing 1 ml of solubilized intestinal submucosal tissue in a 35 mm culture plate, heated at 37° C. for 2 hours, removing the excess intestinal submucosal tissue fluid by aspiration and washing the coated plates once with culture media.

In direct contact culture method, an intestinal submucosa membrane of approximately 1×1 cm was placed on top of stainless steel mesh with the stratum compactum side facing up. Isolated islets were then placed onto the membrane and continuously cultured in M-199 medium (commercially available from Gibco BRL) for 7 days. Cell proliferation was examined every second day under a stereomicroscope and was compared with the control group (cultured in the absence of submucosa tissue).

Sterilization of Submucosal Tissue Before Co-Culturing
 1. Intestinal submucosal tissue derived cell culture substrates were sterilized by several different means: peracetic acid treatment or gamma irradiation. Gamma irradiated and the native (no further treatment after isolation of the intestinal submucosal tissue) membranes can be used directly as cell culture substrates provided they have been sufficiently rehydrated with the culture media prior to the co-culture (native membranes must be cultured in the presence of antibiotics). Peracetic acid sterilized membranes, must first be washed to remove residual peracetic acid prior to culturing since peracetic acid residue may be toxic to the cells. Typically peracetic acid sterilized tissues were soaked in a large quality of medium for 24 hours followed by extensive washing with the same medium.
 2. Solubilized forms of intestinal submucosal tissue were sterilized by dialyzing against 6.5% chloroform in either 0.1M acetic acid (AA-submucosa) or phosphate buffered saline (PBS-submucosa) for 2 hours at room temperature. The exterior surface of the dialysis tubing is sterilized by rinsing the outside of the tubing with 70% alcohol prior to removal of the intestinal submucosal tissue. The dialysis tubing has a molecular weight cut-off of 12,000–14,000; thus, proteins retained inside tubing are those with molecular weight greater than 14,000.

Results

In the control group (islets cultured in the absence of submucosa tissue) examination of seven day cultures revealed that fibroblast cells had overgrown the islet cells.

When islet cells were cultured on growth substrates comprising intestinal submucosal tissue, overgrowth of the islet cells by fibroblast cells did not occur. In intestinal submucosal tissue direct culture systems, the islets became loosely packed with many cells surrounding the islet capsule. Cells migrated from the capsule and cell proliferation occurred on top of the membrane in the absence of fibroblast overgrowth. Culturing islet cells on intestinal submucosal tissue coated culture ware also appeared to facilitate migration of epithelioid cells out of the islet capsule. Further attachment to the coating surface and the formation of a monolayer of epithelioid cells was observed.

These data indicate that submucosal substrates can be used to stimulate growth of islet cells in vitro without overgrowth of fibroblast cells. Islet cells can thus be isolated from pancreatic tissue and grown in vitro in contact with a cell growth substrate comprising intestinal submucosal tissue of a warm-blooded vertebrate under conditions conducive to the proliferation of the islet cells and without concurrent growth of fibroblasts. These islet cell culture compositions remain substantially free of fibroblast overgrowth.

EXAMPLE 7

The ability of intestinal submucosa to augment wound healing and promote tissue remodeling has been previously disclosed. However, certain tissues repair slowly after tissue damage, or have been damaged to such a great extent (for example in burn patients) that submucosal tissue alone fails to provide the desired speed of recovery. The combination of a preselected population of cells with the submucosa matrix has been found to enhance the repair capabilities of the submucosa tissue graft constructs. In one embodiment the submucosa tissue is combined with primary cell cultures specific for damaged or diseased tissues to be repaired in the body. The combination of the preselected population of cells with the submucosa matrix provides an improved tissue graft construct that shows surprising improved wound healing and subsequent better restoration of function when compared to the use of either component alone as a therapeutic agent.

A study was conducted in which the gingiva (gums) and deeper periodontal structures were completely removed from several teeth in a canine model. The defect areas, which extended down to the alveolar bone, were treated with either intestinal submucosa alone, Alloderm (a commercial product derived from human dermis), or a composite of intestinal submucosa plus primary autologous gingiva epithelial cells. Results showed that the sites treated with the composite intestinal submucosa plus primary epithelial cells healed best with an intact epithelial cell population consisting of the cultured epithelial cells and a sub-epithelial connective tissue layer which replaced the missing connective tissue support structures. The sites treated with intestinal submucosa alone or Alloderm formed a more typical scar tissue type response with a lesser epithelial cell component than was seen in the sites treated with the composite structures. This study showed the superior healing of the composite.

In addition, primary esophageal epithelial cells have been grown on an 8-layer intestinal submucosa laminate structure which has shown utility as an esophageal repair device. The preparation of multi-laminate submucosa structures is fully described in U.S. Pat. No. 5,711,969, the disclosure of which is expressly incorporated herein.

EXAMPLE 8

A large study recently completed in pigs shows that intestinal submucosa when used in combination with a split thickness skin graft (which essentially represents an autograft) results in improved "take" rates for the split thickness skin graft (STSG) when compared to use of the STSG alone. This combination intestinal submucosa plus thin STSG fills a specific need in the treatment of full thickness skin wounds: specifically, thin (less than 0.010 inch) STSGs can be harvested and used with the intestinal submucosa carrier to treat these types of wounds instead of needing to harvest a thick (greater than 0.010 inch) STSG which leaves a deep wound at the graft harvest site with significant morbidity and subsequent scarring. This type of study shows the utility of the composite intestinal submucosa plus primary epithelial cells and its superiority over the use of either alone.

EXAMPLE 9

Use of Intestinal Submucosa in the Repair of Articular Cartilage Defects

As articular cartilage has a limited ability for repair, once it has been damaged by trauma or disease, it may deteriorate, resulting in an osteoarthritic joint Although joint replacement with a prosthesis is the treatment of choice, these have a limited lifespan, and replacement of a failed implant is a difficult procedure. Consequently, biological resurfacing has been developed as a way to treat localized, or early cartilage damage in order to delay or preferably prevent the onset of osteoarthritis.

Recently, there has been increasing interest in the transplantation of chondrocytes, either alone or within a carrier into cartilage defects. Early studies demonstrated that isolated chondrocytes were incorporated into defects; however, there was a 28–61% failure rate due to poor fixation. Oversewing the chondrocyte implant with periosteum has increased the success rate, although the technique is technically demanding and may damage the adjacent cartilage. Seeding the chondrocytes within carriers has been used to help improve the retention of cells in the defect. Recent studies by Freed et al. using cartilaginous tissue polyglycolic acid polymer composites to repair defects in rabbits showed promising results, but the defects were in the non-weight-bearing part of the joint and only short-term studies were performed.

Porcine small intestinal submucosa is a resorbable biomaterial that upon implantation induces tissue remodeling. This material was investigated for use as a suitable substratum for the formation of cartilage in vitro, which could then be used to resurface damaged joints. The submucosa—cartilaginous tissue composites were implanted into full thickness articular cartilage defects. After 4 weeks, the composites had survived and retained their hyaline-like appearance, although fibrovascular and fibrocartilaginous tissue was also present. Defects receiving intestinal submucosa alone contained predominantly fibrovascular tissue, whereas ungrafted defects were filled with fibrocartilage. Submucosa-cartilaginous tissue-resurfaced defects scored significantly better than submucosa-filled defects, but were no different from the unfilled defects. However, the repair tissue in the composite-filled defects scored significantly higher than that in the unfilled defects. This pilot study suggests that submucosa-cartilaginous tissue grafts may be useful for joint resurfacing.

In one embodiment chondrocytes are cultured in vitro to forma cell layer on the surface of intestinal submucosa and then implanted to support bone ingrowth while the submucosa is bioabsorbed. Such a construct promotes graft fixation without jeopardizing the integrity of the overlying cartilage.

MATERIALS AND METHODS

Chondrocyte Culture

Intestinal submucosa was prepared as a two-layer woven sheet and was stored at $-20°$ C. One week prior to use, the intestinal submucosa was soaked in three changes of antibiotics (10,000 U/ml penicillin G, 10 mg/ml streptomycin sulphate, 25 µg/ml fungizone; GIBCO BRL, Burlington, Canada), rinsed three times with Ham's F12 (GIBCO BRL) cut into 4-mm discs using a biopsy punch (Premier Medical Products, Norristown, Pa.), and either used for direct implantation or for cell culture.

To obtain chondrocytes, the stifle joints of New Zealand White (NZW) rabbits (male, 2 kg) were opened, and the superficial portion of the articular cartilage was dissected off and discarded. The remaining cartilage (lower third) was harvested and the cells isolated by sequential digestion with 0.25% proteinase (Sigma Chemical Co., St Louis, Mo.) for 1 h, followed by 0.1% collagenase (Collagenase A, Boehringer Mannheim, Laval, Canada) for 4 h.[27] The chondrocytes were resuspended in Ham's F12 supplemented with 5% normal rabbit serum (NRS) and plated on intestinal submucosa ($2\times10^5$ cells/disc of woven sheet Intestinal submucosa). The rabbit serum was obtained by intracardiac puncture of NZW rabbits (University of Toronto, Toronto, Canada), heat inactivated ($60°$ C. for 30 min), and filter sterilized prior to being stored at $-20°$ C.

On day 5, the medium was changed to Dulbecco's modified Eagles medium (DMEM; GIBCO BRL), supplemented with 20% NRS and 100 µg/ml ascorbic acid (AA). The medium was changed every 2–3 days. On day 14, 10 mM β-glycerophosphate (β-GP) was also added to the medium. The cultures were harvested at various time points up to 8 weeks for analysis.

Histological Evaluation of Cultures

Cultures were fixed in 10% formalin and then paraffin embedded. Five-micron sections were stained with H&E to assess cellularity, toluidine blue to assess for the presence of sulfated proteoglycans, or von Kossa to assess for calcification. The thickness of 8-week-old cultures was determined morphometrically using the Q500MC image analysis system (Leica Canada Ltd., Willowdale, Canada). A minimum of 10 points per section and three sections per culture were measured.

DNA and Proteoglycan Quantitation

The amount of DNA and proteoglycan in 8-week-old intestinal submucosa-cartilage cultures, 4-mm discs of Intestinal submucosa, both "as received,"(having been stored at $-20°$ C.) and after 8 weeks in culture, and rabbit deep cartilage were quantitated. Samples were rinsed with PBS and lyophilized, and their dry weights were measured. They were then digested with papain (80 µg/ml in 20 mM ammonium acetate, 1 mM EDTA, 2 mM dithiothreitol; Sigma, St. Louis, Mo.) for at least 18 h at $65°$ C.

The DNA content in the digests was measured using Hoescht 33258 dye (Polysciences Inc., Warrington, Pa.) and fluorometry using techniques known to those skilled in the art. Calf thymus DNA (Pharmacia, Montreal, Canada) in PBS was used to generate the standard curve.

The amount of proteoglycans was estimated by measuring the glycosaminoglycan (GAG) content of the papain digests using the dimethylmethylene blue dye (Polysciences Inc.) binding assay using techniques known to those skilled in the art. The assay was performed in 96-well plates, and the absorbance at 525 nm was measured by an automatic plate reader (Titrek Multiscan, InterSciences Inc., Finland). Chondroitin sulfate (Sigma) was used to generate the standard curve. All values were normalized to dry weight.

The GAG and DNA content of the cartilaginous tissue formed on the intestinal submucosa was estimated by correcting for the intestinal submucosa contribution (submucosa cultured for 8 weeks in the absence of cells).

Proteoglycan Analysis

To examine proteoglycan size, proteoglycans (PG) were extracted from 8-week-old cultures, deep articular cartilage and intestinal submucosa with 4 M guanidine HCl (50 mM sodium acetate, pH 5.8) containing protease inhibitors (5 mM N-ethylmaleimide, 50 mM benzamidine HCl, 10 mM EDTA, 0.1 M6-aminohexanoic acid), and precipitated with three volumes of ice cold ethanol. Thirty micrograms of each sample were separated using a 0.8% submerged horizontal agarose gel. The gels were stained with 0.002% toluidine blue in 0.1 N acetic acid for 30 min and destained with 0.1 N acetic acid.

Collagen Analysis

Representative cultures were labeled with [$^{14}$C]proline (10 µCi/ml, L-[$^{14}$C(U)]proline; Dupont NEN, Boston, Mass.) for 24 h. The collagen was pepsin extracted (100 µg/ml 0.1 N acetic acid; Worthington Biochemical Corp., Freehold, N.Y.) for 24 h at 4° C. The pepsin extracts were separated on a 5% sodium dodecyl sulfate-polyacrylamide gel (SDS-PAGE) and either prepared for autoradiography or transferred to nitrocellulose for Western blot analysis. The presence of type I or type II collagen was determined by Western blot using antibodies reactive with type I collagen (polyclonal; Southern Biotechnology Associates Inc., Birmingham, Ala.) or type II collagen (monoclonal antibody CIICI; Developmental Studies Hybridoma Bank, Baltimore, Md.). Reactivity was detected using affinity purified, secondary antibodies conjugated with alkaline phosphatase (BioRad, Mississauga, Canada). Nitroblue tetrazolium and 5-bromo-4-chloro-3-indolyl phosphate were added for substrate and colour reaction (GIBCO BRL).

In vivo Resurfacing Studies

Thirteen NZW rabbits (females, 4.5 kg) were divided into two groups: seven experimental and six control. The rabbits were anesthetized with Acepromazine (1 mg/kg s.c.) and Somnotol (25 mg/kg i.v.). The stifle joints were exposed using a lateral longitudinal parapatellar incision, and the patella was dislocated. Bilateral incisions were made in the experimental group and a unilateral incision in the control group. A 4-mm diameter defect was made in the articular cartilage of the trochlear groove of the distal femur using a disposable biopsy punch in order to minimize damage to the surrounding cartilage. The defect was then extended into the subchondral bone using an electric drill (Variable speed rotary drill, Sears model no. 924375).

Animals in the experimental group received a intestinal submucosa-cartilaginous tissue transplant in one knee and intestinal submucosa only in the opposite knee. The intestinal submucosa-cartilaginous tissue composites had been in culture for 8 weeks prior to transplantation. The transplants were press-fit into the defect so that the surface of the transplant was level with the articular surface. The defects created in the control group of animals were left unfilled. The patella was reduced, and the capsule and skin were sutured closed. The animals were allowed free activity. Food and water were provided ad libitum. The rabbits were sacrificed at 4 weeks with an overdose of T61 and the knee joints harvested.

Histological Evaluation of the Defects

The distal femurs were fixed in 10% buffered formalin, processed undecalcified in graded ethanols, and plastic embedded in Spurr resin. Five-micron-thick sections were cut and stained either with H&E, or toluidine blue. The histological features were assessed using a scoring method (maximum score=13) adapted from O'Driscoll et al., J. Bone Joint Surg. [Am.] 70-A, 595 (1988) and Ben-Yishay et al., Tissue Eng. 1, 119 (1995) See Table 1. Briefly, the features assessed were (a) the tissue filling the defect (type of tissue, staining characteristics and appearance of the surface of the repair tissue) (b) fusion with the adjacent cartilage and bone, (c) filling of the defect, and (d) whether the adjacent tissue showed degenerative changes. Differentiation between hyaline-like and fibrocartilaginous tissue was based on histological features and whether collagen fibers could be visualized by polarized light microscopy, which is a feature of fibrocartilage. Data were analyzed statistically using the Student's t test and significance was assigned at a p value of <0.05.

TABLE 1

HISTOLOGICAL SCORING SCHEME
FOR REPAIR OF CARTILAGE DEFECTS

| Tissue in defect | |
|---|---|
| Type of the predominant tissue | |
| Hyaline | 3 |
| Hyaline/fibrocartilage | 2 |
| Fibrocartilage | 1 |
| No cartilage | 0 |
| Staining of matrix | |
| Normal | 3 |
| Moderate | 2 |
| Slight | 1 |
| None | 0 |
| Surface | |
| Smooth | 2 |
| Slight disruption | 1 |
| Severe disruption/fibrous | 0 |
| Filling of defect | |
| Equal with adjacent cartilage | 1 |
| Depressed/raised | 0 |
| Fusion to surrounding tissue | |
| Complete | 3 |
| Partial | 2 |
| One side | 1 |
| None | 0 |
| Adjacent cartilage | |
| Normal | 1 |
| Degenerative changes | 0 |
| Maximal score | 13 |

RESULTS

Histological Appearance of Intestinal Submucosa-Cartilaginous Tissue Formed in Vitro The intestinal submucosa-cartilaginous tissue composites were examined histologically after 3, 6, and 8 weeks in culture. The chondrocytes attached to the woven intestinal submucosa, accumulated extracellular matrix, and formed cartilaginous tissue. The chondrocytes were round and in lacunae. The extracellular matrix stained metachromatically with toluidine blue, indicating the presence of sulfated proteoglycans. Some cells had infiltrated into the intestinal submucosa, and these were surrounded by small amounts of matrix. Von Kossa staining revealed the presence of focal deposits of calcification in the cartilaginous tissue matrix adjacent to the intestinal submucosa, and in some cultures these formed a continuous layer of mineral by 8 weeks. By 8 weeks in culture, the cartilaginous tissue had an average thickness of 153.4±60.7 μm (mean±SE).

Quantitation of DNA and Proteoglycan Content of the Cartilaginous Tissue Formed in Vitro The amount of DNA and proteoglycan was measured in 8-week-old intestinal submucosa-cartilage cultures and was compared to the in vivo rabbit deep cartilage (Table 2). The cartilaginous tissue formed on the intestinal submucosa was estimated to contain 0.86±0.2 μg DNA/mg dry weight (mean±SE) and 86.5±5.5 μg GAG/mg dry weight (mean±SE), whereas the rabbit deep cartilage contained 0.83±0.2 μg DNA/mg dry weight (mean±SE) and 109.64±7.8 μg GAG/mg dry weight (mean±SE). Although there was no significant difference in the amount of DNA, there was significantly more GAG present in the in vivo tissue than the cartilaginous tissue formed in vitro ($p=0.03$). The "as received" intestinal submucosa samples had a DNA content of 2.90±0.2 μg/mg dry weight (mean±SE) and a GAG content 25.35±5.0 μg/mg dry weight (mean±SE), whereas the intestinal submucosa analyzed after 8 weeks of culture ("post culture") had DNA and GAG values of 2.04±0.1 and 8.66±0.6 μg/mg dry weight (mean±SE), respectively.

Analysis of the Proteoglycans and Collagen

As large proteoglycans and type II collagen are the major macromolecules present in the matrix of cartilage, the proteoglycan and collagen present in the cartilaginous tissue formed in vitro was analyzed to determine whether the chondrocyte phenotype was retained under these culture conditions. Agarose gel electrophoresis showed that the 8-week intestinal submucosa-cartilage cultures synthesized a population of large proteoglycans that were similar in size to those extracted from rabbit deep articular cartilage, although some of the proteoglycans were larger than those extracted from the in vivo tissue. Proteoglycans extracted from intestinal submucosa were much smaller and ran as two broad bands near the bottom of the gel.

Pepsin extracts of 8-week intestinal submucosa-cartilaginous tissue composites were analyzed by SDS-PAGE and autoradiography. A band similar in size to the $\alpha_1$ (I) chain of type II collagen was seen. No band, corresponding to $\alpha_2$ chain of type I collagen, was present. A higher molecular weight band, likely representing dimers of the $\alpha 1(H)$ chains, was also present. Western blot analysis of these extracts confirmed the presence of type II collagen. Type I collagen was detected in both the pepsin extracts of intestinal submucosa-cartilaginous tissue composites and from intestinal submucosa alone. No type II collagen was detected in the intestinal submucosa extracts by Western blot analysis.

TABLE 2

DNA AND GLYCOSAMINOGLYCAN QUANTITATION

| Tissue | Dry weight (mg) | DNA (mg/ mg dry weight) | GAG (mg/ mg dry weight) |
|---|---|---|---|
| Rabbit deep cartilage | Na[a] | 0.83 ± 0.2 | 109.64 ± 7.8[b] |
| Intestinal submucosa "as received" | 0.65 ± 0.02 | 2.90 ± 0.2 | 25.35 ± 5.0 |
| Intestinal submucosa "post culture" | 0.43 ± 0.02 | 2.04 ± 0.1 | 8.66 ± 0.6 |
| Intestinal submucosa-cartilaginous tissue | 2.33 ± 0.3 | 1.14 ± 0.2 | 70.65 ± 4.0 |
| Cartilaginous tissue in vitro | 1.90 ± 0.6 | 0.86 ± 0.2 | 86.46 ± 5.5[b] |

[a]NA = not applicable. The pieces of rabbit deep cartilage analyzed ranged from 1.37 to 3.65 mg.
[b]Significant difference between rabbit deep cartilage and cartilaginous tissue in vitro ($p = 0.03$).

The dry weight, and the amount of DNA and glycosaminoglycan (GAG) were determined as described in Materials and Methods. The data for the cartilaginous tissue formed in vitro were estimated by subtracting the mean dry weight or mean total DNA and GAG for intestinal submucosa after 8 weeks in culture ("post culture"), from the dry weight and total DNA and GAG respectively of each Intestinal submucosa-cartilaginous tissue sample. The analysis was performed on at least two different samples from each of three different experiments. The data are expressed as mean±SE.

In Vivo Studies

The joints of animals that had received intestinal submucosa-cartilaginous tissue grafts showed no synovial effusion, although in two rabbits the joints were enlarged due to the presence of osteophytes. The defects were all filled with white tissue, and the adjacent cartilage appeared normal in five joints and fibrillated in two.

Of the seven animals for which intestinal submucosa alone had been used to repair the defect, four developed osteophytes; and one had a synovial effusion. One animal developed a unilateral septic arthritis with a purulent effusion, and the joint was eliminated from the study. The defects in the remaining six rabbits were filled with whitish granular tissue. The adjacent cartilage showed signs of degeneration in all but one animal.

Of the six rabbits that received no transplant, four of the joints were unremarkable grossly and two had synovial effusions. No osteophytes were seen. All the defects were filled with a white tissue, and no degeneration of the adjacent cartilage was visible.

Histological examination of the defects that had received intestinal submucosa-cartilaginous tissue transplants showed that graft tissue was present in six of seven defects. The grafts maintained their appearance of hyaline cartilage. All the transplants were surrounded by variable amounts of fibrovascular tissue towards the joint surface and fibrocartilage tissue above or below the implant. When the graft approximated the adjacent host cartilage or bone, there was fusion between the two tissues. Fusion between the transplant and the under lying fibrocartilage also occurred. The one defect from which the graft had fallen out was filled entirely with fibrocartilage.

Histologically, the defects that received intestinal submucosa grafts were filled with fibrovascular tissue. There was no or minimal amounts of fibrocartilage. If fibrocartilage was present, it was present at the edge of the defect. Residual intestinal submucosa was only seen in one defect. Although the articular cartilage surrounding the defect merged with the fibrovascular tissue filling the defect, it was possible to distinguish the margins of the articular cartilage from the reparative tissue. In contrast, the joint defects that had not received a transplant were entirely filled with fibrocartilage, which showed variable amounts of bonding to the adjacent cartilage and bone. The fibrocartilage could be easily differentiated from the adjacent articular cartilage as it was more cellular, the matrix was fibrous in appearance, and collagen fibers could be visualized under polarized light. The surface of the fibrocartilage showed degenerative changes with loss of proteoglycans.

Scoring the histological appearance of the defects (Table 3) demonstrated that the joints resurfaced with the intestinal submucosa-cartilaginous tissue grafts or which had received no transplant were significantly better than those which had been implanted with intestinal submucosa alone (p=0.004). There was no difference between the histological scores of the intestinal submucosa-cartilaginous tissue transplanted group and those defects that were left unfilled. However, comparison of the scores obtained for tissue type and staining of the repair tissue in the defect showed that the intestinal submucosa-cartilaginous tissue grafted group was significantly better than that of the no graft group (p=0.019).

TABLE 3

HISTOLOGICAL SCORES OF DEFECTS

| Graft | Type and staining of tissue in defect[a] | Total[b] |
|---|---|---|
| Intestinal submucosa-cartilaginous tissue | 3.7 ± 0.8[d] | 6.1 ± 1.2[c] |
| Intestinal submucosa | 1.0 ± 0.7 | 3.8 ± 0.8[c] |
| None | 2.6 ± 0.6[d] | 6.2 ± 0.8 |

[a]Values out of 6 points, expressed as mean ± SD.
[b]Values out of a total of 13 points, expressed as mean ± SD.
[c]Significant difference between Intestinal submucosa-cartilaginous tissue and intestinal submucosa graft (p = 0.004).
[d]Significant difference between Intestinal submucosa-cartilaginous tissue graft and no graft (p = 0.019).

DISCUSSION

Rabbit chondrocytes attached to Intestinal submucosa, accumulated extracellular matrix, and formed cartilaginous tissue in vitro. The chondrocytes under these conditions maintain their phenotype and synthesize large proteoglycans and type II collagen, macromolecules characteristic of hyaline cartilage. There was mineralization of the extracellular matrix near the Intestinal submucosa. In contrast to the cartilaginous tissue formed by chondrocytes obtained from the deep zone of bovine articular cartilage that consistently showed a continuous layer of mineralization when cultured on filter inserts, the tissue on the intestinal submucosa more commonly had only focal areas of mineralization. This discontinuous mineralization was also observed when rabbit deep chondrocytes were cultured on filter inserts (data not shown) suggesting that intestinal submucosa was not affecting tissue mineralization. One explanation for the variation in the extent of mineralization may be due to the difference in the in vivo cartilage thickness between the rabbit and calf. Bovine cartilage is much thicker, and isolation of the deep cells is less likely to be contaminated with chondrocytes from the superficial and mid portion of the cartilage. This is supported by the finding that the rabbit chondrocytes did not synthesize detectable amounts of type I collagen, unlike chondrocytes isolated from the deep zone of bovine cartilage, but similar to chondrocytes isolated from the full thickness of cartilage. Type I collagen was detected by Western blot, but was not seen on autoradiographs suggesting that the type I Collagen was derived from the Intestinal submucosa. However, it is possible that small amounts of newly synthesized collagen were not detected by autoradiography.

The thickness of the cartilaginous tissue that formed on the intestinal submucosa in vitro appeared to be influenced by the method of intestinal submucosa processing (data not shown). intestinal submucosa woven into a sheet supported cartilaginous tissue formation most consistently, which is why it was used in these experiments. When chondrocytes were placed on intestinal submucosa processed in the standard way, there were areas of the mucosal surface of the intestinal submucosa that had thin or no cartilage formation. As the seeding density of chondrocytes is critical for maintenance of chondrocyte phenotype and matrix synthesis, and as the nonwoven intestinal submucosa curled or provided an irregular surface, it is likely that the initial distribution of cells over the surface of the intestinal submucosa was uneven, which may explain the variability.

Comparison of the cartilaginous tissue formed in vitro with the rabbit deep cartilage demonstrated that, while there was no difference in the amount of DNA, the amount of GAG in the cartilaginous tissue was approximately 79% of the in vivo tissue. It is possible that this difference was due to the way in which the contribution of the intestinal submucosa to the composite was determined. intestinal submucosa that had been stored at −20° C. upon receipt ("as received") was found to contain approximately 25 μg GAG per mg dry weight similar to values obtained by Hodde et al.[33] However, intestinal submucosa cultured for 8 weeks in the absence of cells lost 66% of its initial dry weight and the GAG content declined from 2.5% to 0.8% of the dry weight. To estimate the GAG content of the cartilaginous tissue formed on the intestinal submucosa, we assumed that the composition of intestinal submucosa in the intestinal submucosa-cartilage culture was similar to that of the intestinal submucosa after 8 weeks of cell free culture. However, as chondrocytes can produce a variety of matrix degrading enzymes, it is possible that the amount of intestinal submucosa remaining was overestimated. Alternatively, as the intestinal submucosa-cartilaginous tissue composite became thicker, it is possible that nutrient diffusion was limited, which may have influenced chondrocyte biosynthesis and matrix accumulation.

The size of the proteoglycan population synthesized by the chondrocytes cultured on intestinal submucosa overlapped that isolated from deep articular cartilage. However, the in vitro population also contained larger proteoglycans. In a previous study, rabbit chondrocytes cultured on extracellular matrices were stimulated to synthesize larger proteoglycans than when they were cultured on tissue culture polystyrene. Furthermore, intestinal submucosa contains fibroblast growth factor (FGF-2) and transforming growth factor β (TGF-β) related protein, both of which have been shown to stimulate chondrocytes to synthesize larger proteoglycans. It is therefore possible that the intestinal submucosa influenced the chondrocytes to synthesize larger proteoglycans in vitro.

Although the joint defects resurfaced with intestinal submucosa—cartilaginous tissue composites contained viable transplants, the repair was not optimal at 1 month. This was likely due to technical reasons, including inadequate graft fixation, which resulted in pannus formation. Good graft fixation is considered critical for graft incorporation. Although pressfit as a method of fixation has been used by others, in this study it resulted in the grafts having a concave geometry in the defect. The pannus that formed may then have further exacerbated the problem. It is possible that other methods of fixation might result in better graft incorporation. For example, in one study, perichondral grafts were sutured to a bone core and then pressfit into a defect. Using this approach to provide the intestinal submucosa with a more rigid support may keep the transplant level with the adjacent cartilage surface.

Although there was no difference in the overall histological scores between the intestinal submucosa-cartilaginous tissue transplanted defects and the unfilled self-repaired defects, the score obtained for the type and staining of the tissue in the defect was significantly higher in the intestinal submucosa-cartilaginous tissue group. This was due to the hyaline-like appearance of the transplant, while the unfilled defects contained only fibrocartilaginous repair tissue. Fibrocartilage is considered inferior as it undergoes degeneration over time.

The intestinal submucosa alone, when placed in the defects, was not replaced by bone, although 1 month may have been too short a period of time for this to occur. The absence of fibrocartilage filling of the defect, as was seen in the ungrafted defect, suggests that intestinal submucosa may be inhibiting or preventing the formation of this tissue. It is well accepted that, when a joint defect breaches the subchondral bone, the mesenchymal stem cells present in the marrow infiltrate into the defect and differentiate to produce fibrocartilaginous repair tissue.[1,3,42] It is possible that the intestinal submucosa acted as a barrier preventing this infiltration.

In summary, intestinal submucosa supports the formation of cartilaginous tissue in vitro. intestinal submucosa-cartilaginous tissue grafts survive upon transplantation into a joint and are able to fuse with the adjacent cartilage.

The invention claimed is:

1. An improved tissue graft construct comprising
   vertebrate submucosa delaminated from both the external smooth muscle layers and the luminal portions of the tunica mucosa and
   exogenously added primary cells wherein the primary cells are mesenchymal cells.

2. The improved tissue graft construct of claim 1 wherein the vertebrate submucosa comprises tunica submucosa delaminated from both the tunica muscularis and at least the luminal portion of the tunica mucosa of vertebrate intestinal tissue.

3. The improved tissue graft construct of claim 1 wherein the submucosa is fluidized submucosa.

4. The improved tissue graft construct of claim 3 wherein the fluidized submucosa comprises submucosa digested with an enzyme for a period of time sufficient to solubilize the submucosa.

5. An improved tissue graft construct comprising
   tunica submucosa delaminated from both the tunica muscularis and at least the luminal portion of the tunica mucosa of vertebrate intestinal tissue, and
   an exogenously added population of mesenchymal cells.

6. The improved tissue graft construct of claim 5 wherein the submucosa tissue is fluidized submucosal tissue.

7. The improved tissue graft construct of claim 6 wherein the fluidized submucosal tissue comprises submucosal tissue digested with an enzyme for a period of time sufficient to solubilize the tissue.

8. An improved tissue graft construct comprising
   tunica submucosa delaminated from both the tunica muscularis and at least the luminal portion of the tunica mucosa of vertebrate submucosa tissue, and
   an exogenously added population of mesenchymal cells.

9. The improved tissue graft construct of claim 8 wherein the submucosa tissue is fluidized submucosal tissue.

10. The improved tissue graft construct of claim 9 wherein the fluidized submucosal tissue comprises submucosal tissue digested with an enzyme for a period of time sufficient to solubilize the tissue.

11. An improved tissue graft construct comprising
    tunica submucosa delaminated from both the tunica muscularis and at least the luminal portion of the tunica mucosa of vertebrate intestinal tissue, and
    an exogenously added population of cells selected from the group consisting of keratinocytes and mesenchymal cells.

12. An improved tissue graft construct comprising
    vertebrate submucosa delaminated from both the external smooth muscle layers and the luminal portions of the tunica mucosa and
    exogenously added primary cells selected from the group consisting of keratinocytes, chondrocytes, epithelial cells, and mesenchymal cells.

13. An improved tissue graft construct comprising
    tunica submucosa delaminated from both the tunica muscularis and at least the luminal portion of the tunica mucosa of vertebrate submucosa tissue, and
    an exogenously added population of cells selected from the group consisting of keratinocytes and mesenchymal cells.

14. An improved tissue graft construct comprising
    vertebrate intestinal submucosa delaminated from both the external smooth muscle layers and the luminal portions of the tunica mucosa and
    exogenously added primary cells selected from the group consisting of keratinocytes, chondrocytes, epithelial cells, and mesenchymal cells.

15. An improved tissue graft construct comprising
    vertebrate intestinal submucosa delaminated from both the external smooth muscle layers and the luminal portions of the tunica mucosa and
    an exogenously added population of cells selected from the group consisting of keratinocytes, chondrocytes, epithelial cells, and mesenchymal cells.

16. An improved tissue graft construct comprising
    vertebrate submucosa tissue delaminated from both the external smooth muscle layers and the luminal portions of the tunica mucosa and
    an exogenously added population of cells selected from the group consisting of keratinocytes, chondrocytes, epithelial cells, and mesenchymal cells.

* * * * *